US007767224B2

(12) United States Patent
Kummer et al.

(10) Patent No.: US 7,767,224 B2
(45) Date of Patent: Aug. 3, 2010

(54) METHOD FOR THE CONTINUOUS PRODUCTION AND COATING OF SELF-ADHESIVE COMPOUNDS ON THE BASIS OF SBC THAT INCLUDES AT LEAST ONE PHARMACEUTICALLY ACTIVE SUBSTANCE

(75) Inventors: Andreas Kummer, Hamburg (DE); Matthias Wasner, Hamburg (DE); Jens-Uwe Wüstling, Hamburg (DE)

(73) Assignee: Beiersdorf AG, Hamburg (DE)

( * ) Notice: Subject to any disclaimer, the term of this patent is extended or adjusted under 35 U.S.C. 154(b) by 558 days.

(21) Appl. No.: 10/484,816

(22) PCT Filed: Jul. 31, 2002

(86) PCT No.: PCT/EP02/08518

§ 371 (c)(1),
(2), (4) Date: Aug. 18, 2004

(87) PCT Pub. No.: WO03/011260

PCT Pub. Date: Feb. 13, 2003

(65) Prior Publication Data

US 2005/0019382 A1 Jan. 27, 2005

(30) Foreign Application Priority Data

Jul. 31, 2001 (DE) ................. 101 37 405

(51) Int. Cl.
*A61F 13/02* (2006.01)
(52) U.S. Cl. .............. 424/449; 424/484; 424/486; 523/1
(58) Field of Classification Search ......... 424/448, 424/449, 443, 484–486; 523/1; 524/700, 524/555, 558; 528/48
See application file for complete search history.

(56) References Cited

U.S. PATENT DOCUMENTS

| 4,622,260 A | | 11/1986 | Tesch |
| 5,183,705 A | * | 2/1993 | Birkholz et al. ............. 428/343 |
| 5,464,610 A | | 11/1995 | Hayes, Jr. et al. |
| 5,539,033 A | | 7/1996 | Bredahl et al. |
| 5,550,175 A | | 8/1996 | Bredahl et al. |
| 5,869,087 A | * | 2/1999 | Hirano et al. ............... 424/449 |
| 5,876,855 A | * | 3/1999 | Wong et al. ........... 428/355 BL |
| 5,914,157 A | | 6/1999 | Munson et al. |
| 6,277,400 B1 | | 8/2001 | Horstmann et al. |
| 6,319,510 B1 | | 11/2001 | Yates |
| 6,416,749 B1 | | 7/2002 | Hayes, Jr. et al. |
| 6,436,433 B1 | | 8/2002 | Müller |
| 6,555,130 B2 | | 4/2003 | Wüstling et al. |
| 2003/0082227 A1 | | 5/2003 | Sournac et al. |
| 2003/0099695 A1 | | 5/2003 | Mueller |
| 2004/0052835 A1 | | 3/2004 | Klokkers et al. |

FOREIGN PATENT DOCUMENTS

| DE | 19806609 | 8/1999 |
| DE | 10001546 | 7/2001 |
| EP | 0071212 | 2/1983 |
| EP | 1116763 | 7/2001 |
| WO | 94/11175 | 5/1994 |
| WO | 95/25774 | 9/1995 |
| WO | 97/07963 | 3/1997 |
| WO | 98/34600 | 8/1998 |
| WO | 98/36740 | 8/1998 |
| WO | 00/62764 | 10/2000 |
| WO | 01/39754 | 6/2001 |
| WO | 01/68060 | 9/2001 |
| WO | 02/03970 | 1/2002 |

\* cited by examiner

*Primary Examiner*—Michael G Hartley
*Assistant Examiner*—Micah-Paul Young
(74) *Attorney, Agent, or Firm*—Greenblum & Bernstein P.L.C.

(57) ABSTRACT

A process for the solvent-free and mastication-free production of a self-adhesive composition which is based on SBC and comprises a pharmaceutically active substance, in a continuously operating apparatus which comprises a feeding section and a compounding section. The SBC is added to the feeding section and the pharmaceutically active substance is added to the feed section and/or the compounding section, and the composition is homogenized in the compounding section.

50 Claims, 1 Drawing Sheet

METHOD FOR THE CONTINUOUS PRODUCTION AND COATING OF SELF-ADHESIVE COMPOUNDS ON THE BASIS OF SBC THAT INCLUDES AT LEAST ONE PHARMACEUTICALLY ACTIVE SUBSTANCE

CROSS-REFERENCE TO RELATED APPLICATIONS

The present application is a U.S. National Stage of International Application No. PCT/EP02/08518, filed Jul. 31, 2002, which claims priority under 35 U.S.C. §119 of German Patent Application No. 101 37 405.4, filed Jul. 31, 2001.

BACKGROUND OF THE INVENTION

1. Field of the Invention

The present invention relates to a method for the continuous production and coating of self-adhesive compositions based on SBC with at least one pharmaceutically active substance.

2. Discussion of Background Information

Fundamental to the profile of performance requirements of pressure sensitive adhesive systems and the pressure sensitive adhesive articles produced with them (such as patches, for example) are the two physical phenomena of adhesion and cohesion of the pressure sensitive adhesive layers. Adhesion is dealt with in the technical jargon using the terms instant bond strength (tack) and bond strength (peel strength) and describes by definition the terms "self-adhesive", "pressure sensitive adhesive" and/or "pressure sensitive adhesive tapes", i.e., permanent adhesive bonding under "gentle applied pressure".

Especially in the case of pressure sensitive adhesives based on rubber, this property is obtained by mixing in tackifying resins (tackifiers) and plasticizers having relatively low molecular weights.

The second defining property of the pressure sensitive adhesives is their simple residue-free redetachability after use. This property is determined essentially by the high molecular mass rubber fractions as the elastomer component, which give the system, in the form of cohesion (internal strength), the required strength under shear stress, which is of particular significance for the use of the products under mechanical load.

The performance of the pressure sensitive adhesive is, therefore, critically determined by the balanced proportion of adhesion properties and cohesion properties and by compatibility, homogeneity, and stability of the blend of components with extremely high and relatively low average molecular weights, something which is relatively easy to achieve when the composition is produced in industry-standard mixers and kneading machines using solvents.

The advantage of foregoing the use of solvents lies essentially in the simplification of the coating method. The avoidance of flammable solvents does away with the need for the drier units, with their high energy consumption for the evaporation and recovery of the solvents, and with the need to use explosion-protected units. Hot-melt coating units are compact and permit much higher coating speeds. The technology is an environment-friendly one in which there are no solvent emissions. Furthermore, no unwanted solvent residues remain in the self-adhesive composition. This is the reason for the reduction in the allergenic potential of the product.

For solvent-free compounding, the prior art makes use predominantly of block copolymers having polystyrene block fractions, or natural and/or synthetic rubbers.

Owing to the high molecular mass fractions of the rubber (with $M_W \geq 3*10^5$ g/mol), solvent-free natural rubber self-adhesive compositions cannot be processed by the hot-melt pressure sensitive adhesive technology, or else the rubbers used must be reduced in their molecular weight (broken down) severely before processing.

The deliberate industrial process of rubber breakdown under the combined action of shear stress, temperature, and atmospheric oxygen is referred to in the technical literature as mastication and is generally carried out in the presence of chemical auxiliaries, which are known from the technical literature as masticating agents or peptizers, or, more rarely, as "chemical plasticizing agents".

In rubber technology, the mastication step is necessary in order to make it easier to integrate the additives.

Mastication is a term used in rubber technology for the breaking down of long-chain rubber molecules in order to increase the plasticity and/or reduce the (Mooney) viscosity of rubbers. Mastication is carried out by treating, in particular, natural rubber in kneading apparatus or between rolls at very low temperatures in the presence of mastication aids (masticating auxiliaries). The high mechanical forces which act lead to a "tearing apart" of the rubber molecules, with the formation of macroradicals, whose recombination is prevented by reaction with atmospheric oxygen. Mastication aids such as aromatic or heterocyclic mercaptans and their zinc salts or disulfides accelerate the mastication process by promoting the formation of primary radicals. Activators such as metal (iron, copper, cobalt) salts of tetraazaporphyrins or phthalocyanines enable the mastication temperature to be lowered. For the mastication of natural rubber, mastication aids are used in amounts of from about 0.1 to 0.5% by weight in the form of masterbatches, which facilitate a uniform distribution of this small amount of chemicals within the rubber composition.

Mastication must be clearly distinguished from the breakdown known as degradation which results in all of the standard solvent-free polymer technologies, such as compounding, conveying, and coating in the melt.

Degradation is a collective term for various processes which change the appearance and properties of plastics. Degradation may be caused, for example, by chemical, thermal, oxidative, mechanical or biological influences or else by the effect of rays (such as (UV) light). Examples of consequences are oxidation, chain cleavages, depolymerization, crosslinking, and/or elimination of side groups of the polymers. The stability of polymers with respect to degradation may be increased by using additives, for example, by adding stabilizers such as antioxidants or light stabilizers.

A variety of routes to the solvent-free production and processing of rubber pressure sensitive adhesives have been described.

The patent CA 698 518 describes a process for producing a composition by adding high proportions of plasticizer and/or by simultaneously strong mastication of the rubber. Although this method may be used to obtain pressure sensitive adhesives having an extremely high tack, a user-compatible shear strength can be achieved only to a limited extent, even with a relatively high level of subsequent crosslinking, owing to the relatively high plasticizer content or else to the severe breakdown in molecular structure of the elastomer to a molecular weight average of $M_W \leq 1$ million.

The use of polymer blends, where, besides nonthermoplastic natural rubber, use is also made of block copolymers, in a ratio of approximately 1:1, is essentially an unsatisfactory compromise solution, since it results neither in high shear strengths when the self-adhesive tapes are used at relatively high temperatures nor in significant improvements relative to the properties described in the patent.

The use of exclusively non-thermoplastic rubbers as the elastomer component in the formulation of pressure sensitive adhesives with the existing cost advantage possessed by, for example, natural rubbers over the standard commercial block copolymers, and the outstanding properties, especially the shear strength of natural rubber and of corresponding synthetic rubbers, is also set out at length in the patents WO 94 11 175 A1, WO 95 25 774 A1, and WO 97 07 963 A1 and, correspondingly, U.S. Pat. Nos. 5,539,033 A and 5,550,175 A.

In these cases, the additives customary in pressure sensitive adhesive technology, such as tackifier resins, plasticizers, and fillers, are described.

The production method disclosed in each case is based on a twin screw extruder which permits compounding to a homogeneous pressure sensitive adhesive blend with the chosen process regime, involving mastication of the rubber and subsequent gradual addition of the individual additives with an appropriate temperature regime.

The mastication step of the rubber, which precedes the actual production process, is described at length. It is necessary and characteristic of the process chosen, since with the technology chosen therein it is indispensable to the subsequent integration of the other components and to the extrudability of the blended composition. Also described is the feeding in of atmospheric oxygen, as recommended by R. Brzoskowski, J. L. and B. Kalvani in Kunststoffe 80 (8), (1990), p. 922 ff., in order to accelerate mastication of the rubber.

This procedure makes it absolutely necessary to practice the subsequent step of curing by electron beam crosslinking (EBC) and to use reactive substances as EBC promoters in order to achieve an effective crosslinking yield.

Both method steps are described in the abovementioned documents, but the EBC promoters chosen also tend toward unwanted chemical crosslinking reactions at elevated temperatures. This limits the use of certain tackifying resins and the use of the self-adhesive compositions produced, in particular for pharmaceutical applications.

It is an object of the present invention to provide a method with which self-adhesive compositions based on SBC and comprising at least one active pharmaceutical substance can be produced continuously without solvent and, if desired, can be coated in-line without the need for property-impairing mastication of the SBC.

SUMMARY OF THE INVENTION

The present invention provides a process for the solvent-free and mastication-free production, in a continuously operating apparatus which comprises a feeding section and a compounding section, of an SBC-based self-adhesive composition which comprises at least one pharmaceutically active substance. This process comprises (a) feeding an initial batch which comprises the SBC, at least a part of the at least one pharmaceutically active substance and, optionally, at least a part of any further components of the composition into the feeding section of the apparatus;

(b) transferring the initial batch from the feeding section to the compounding section of the apparatus;

(c) optionally, adding any remaining part of the at least one pharmaceutically active substance and any remaining part of the further components of the composition which have not been added to the feeding section, to the compounding section;

(d) treating the composition in the compounding section to prepare a homogeneous self-adhesive composition; and (e) discharging the homogeneous self-adhesive composition from the apparatus.

Alternatively, the process of the present invention comprises the addition of the at least one pharmaceutically active substance in its entirety to the compounding section of the apparatus.

In one aspect of the above processes, the further components of the composition may be selected from one or more of low molecular weight SBCs, fillers, plasiticizers, tackifiers, resins, release aids and additives.

In another aspect, the apparatus may comprise a twin-screw extruder. By way of non-limiting example, the twin-screw extruder may comprise at least one metering port (preferably from two to seven metering ports) and at least one degassing port.

In yet another aspect, the temperature inside the apparatus may be from 85° C. to 120° C., for example, from 85° C. to 110° C., or from 85° C. to 100° C.

In a still further aspect of the processes of the present invention, the at least one pharmaceutically active substance may be used in a concentration of from 0.001% to 0.70% by weight, based on the weight of the composition, preferably in a concentration of from 0.01% to 0.67% by weight, even more preferred, in a concentration of from 0.03% to 0.63% by weight.

In another aspect, the SBC may be used in a concentration of from 5% to 90% by weight, such as, e.g., in a concentration of from 10% to 85% by weight.

The present invention also provides a self-adhesive composition which is obtainable by the processes of the present invention, including the various aspects thereof.

The present invention also provides a process for producing a self-adhesive composition on a carrier material. This process comprises carrying out any of the processes set forth above, including the various aspects thereof, transferring the self-adhesive composition to a coating device and thereafter, coating the carrier material with the self-adhesive coating composition.

In one aspect, the transfer of the coating composition to the coating device may involve a melt pump and/or an extruder.

In another aspect, the carrier material may comprise a web material and/or a release film and/or a release paper.

In yet another aspect, the process may further comprise the covering of the coated composition with a release film or release paper.

In a still further aspect, the coating device may comprises an extrusion die, a roll unit and/or a calender unit, or an extrusion die plus a roll unit and/or a calender unit. For example, the coating thickness of the composition may be adjusted by allowing it to pass through one or more roll nips of the roll unit and/or the calender unit. In this regard, according to another aspect of the process, the thickness of the self-adhesive composition on the carrier material may be adjusted to from 10 µm to 2,000 µm, for example, from 20 µm to 500 µm, or from 50 µm to 400 µm.

The present invention also provides a self-adhesive composition on a carrier material which is obtainable by the process set forth above, including the various aspects thereof.

In the compounding step, an adhesive composition comprising styrene block copolymers, one or more active pharmaceutical substances, and the required adjuvants such as low molecular mass SBC, fillers, plasticizers, tackifiers, resins and/or additives, is produced without solvent preferably in a twin screw extruder. The active pharmaceutical substances here may be added directly at the beginning of the method, but may also—depending on the sensitivity of the active substance—be introduced into the twin screw extruder only at a later point in time. The addition may be made in neat or dissolved form.

In accordance with the invention, the hot-melt self-adhesive composition in which at least one active pharmaceutical substance is incorporated, is based on
- phase-separating styrene block copolymers,
- tackifying resins,
- tackifiers,
- plasticizers,
- fillers and/or additives.

Suitable styrene block copolymers include preferably A-B and/or A-B-A block copolymers or mixtures thereof. The hard, domain-forming phase A consists primarily of polystyrene or derivatives thereof. The soft phase is formed primarily from polyisoprene and polybutadiene or mixtures thereof. The phase-separating structure of the styrene block copolymers helps the polymers have a thermoplastic behavior which differs from that of polymers containing randomly distributed monomers and ensures mastication-free processing. Owing to the incompatibility of the A blocks and B blocks, the block copolymers possess two glass transition temperatures $T_g$: as a result of the B blocks, a low $T_g$, below room temperature, and, as a result of the styrene blocks, a high $T_g$, above room temperature. In the temperature range between the two glass transition temperatures the block copolymers exhibit on the one hand elastic behavior as a result of the B blocks, but on the other hand the rubber remains cohesive as a result of the hard styrene domains, which come about as a result of secondary valence forces of the styrene blocks.

The fraction of the styrene block copolymers is between 5 and 90% by weight, preferably between 10 and 85% by weight.

Suitable fillers are free-flowing bulk materials and also mixtures thereof, such as cellulose, silica, alginates and pectins, which are not soluble in the adhesive matrix.

The filler fraction is in particular between 0% by weight and 60% by weight, preferably between 0% by weight and 40% by weight, with particular preference between 0% by weight and 30% by weight.

Tackifying resins which can be used are, without exception, all tackifier resins known to date and described in the literature. Representatives that may be mentioned include the rosins, their disproportionated, hydrogenated, polymerized and esterified derivatives and salts, the aliphatic and aromatic hydrocarbon resins, terpene resins and terpene-phenolic resins. Any desired combinations of these and other resins can be used in order to adjust the properties of the resultant adhesive composition in accordance with what is desired. Reference may be made expressly to the depiction of the state of knowledge in "Handbook of Pressure Sensitive Adhesive Technology" by Donatas Satas (van Nostrand, 1989).

The resin fraction is in particular between 0% by weight and 80% by weight, preferably between 0% by weight and 60% by weight, with particular preference between 10% by weight and 50% by weight.

Hydrocarbon resin is a collective term for thermoplastic polymers which are colorless to intense brown in color and have a molar mass of generally <2 000.

They may be divided into three main groups according to their provenance: petroleum resins, coal tar resins, and terpene resins. The most important coal tar resins are the coumarone-indene resins. The hydrocarbon resins are obtained by polymerizing the unsaturated compounds that can be isolated from the raw materials.

Included among the hydrocarbon resins are also polymers obtainable by polymerizing monomers such as styrene and/or by means of polycondensation (certain formaldehyde resins), with a correspondingly low molar mass. Hydrocarbon resins are products with a softening range that varies within wide limits from <0° C. (hydrocarbon resins liquid at 20° C.) to >200° C. and with a density of from about 0.9 to 1.2 g/cm$^3$.

They are soluble in organic solvents such as ethers, esters, ketones, and chlorinated hydrocarbons, and insoluble in alcohols and water.

By rosin is meant a natural resin which is recovered from the crude resin from conifers. Three types of rosin are differentiated: balsam resin, as a distillation residue of turpentine oil; root resin, as the extract from conifer rootstocks; and tall resin, the distillation residue of tall oil. The most significant in terms of quantity is balsam resin.

Rosin is a brittle, transparent product with a color ranging from red to brown. It is insoluble in water but soluble in many organic solvents such as (chlorinated) aliphatic and aromatic hydrocarbons, esters, ethers, and ketones, and also in plant oils and mineral oils. The softening point of rosin is situated in the range from approximately 70 to 80° C.

Rosin is a mixture of about 90% resin acids and 10% neutral substances (fatty acid esters, terpene alcohols, and hydrocarbons). The principal rosin acids are unsaturated carboxylic acids of empirical formula $C_{20}H_{30}O_2$, abietic acid, neoabietic acid, levopimaric acid, pimaric acid, isopimaric acid, and palustric acid, as well as hydrogenated and dehydrogenated abietic acid.

The proportions of these acids vary depending on the provenance of the rosin.

Suitable tackifiers are all known tackifying polymers, from the group, for example, of the polyisoprenes and polybutadienes. The tackifier fraction is in particular between 0% by weight and 50% by weight, preferably between 0% by weight and 40% by weight, with particular preference between 0% by weight and 30% by weight.

Plasticizers which can be used are all known plasticizing substances and also pharmaceutical auxiliaries. They include, inter alia, the paraffinic and naphthenic oils, (functionalized) oligomers such as oligobutadienes and oligoisoprenes, liquid nitrile rubbers, liquid terpene resins, vegetable and animal oils and fats, fatty acid esters, phthalates, alcohols, and functionalized acrylates.

The plasticizer fraction is in particular between 0% by weight and 60% by weight, preferably between 2% by weight and 40% by weight.

Additives used can include aging inhibitors or stabilizers. There include, for example, sterically hindered phenols, hydrolysis-stable phosphites and organosulfur compounds. The additive fraction is between 0% and 5% by weight, preferably between 0% and 3% by weight.

Active pharmaceutical substances are substances which in human or animal organisms are used to prevent, heal, alleviate or detect diseases. The active pharmaceutical substances used may include those having both systemic and local activity.

Typical active substances used in accordance with the invention are the following: aceclidine, amphetaminil, amphetamine, amyl nitrite, apophedrine, atebrine, alprostadil, azulene, arecoline, anethole, amylene hydrate, acetylcholine, acridine, adenosine-triphosphoric acid, malic acid, alimemazine, allithiamine, aminoethanol, apyzine, apiole, azatadine, alprenolol, ethinazone, bisabolol, bisnorephedrine, butacetoluide, benactyzine, camphor, colecalciferol, chloral hydrate, clemastine, chlorobutanol, capsaicin, cyclopentamine, clobutinol, chamazulene, dimethocaine, codeine, chlorpromazine, quinine, chlorothymol, cyclophosphamide, cinchocaine, chlorambucil, chlorphenesin, dexchlorpheniramine, dinoprostone, dixyrazine, ephedrine, ethosuximide, enallylpropymal, emylcamate, erythrol tetranitrate, emetine, eucalyptol, etofenamate, ethylmorphine, fentanyl, fluanisone, guaiazulene, hyoscyamine, histamine, fencarbamide, hydroxycaine, hexylresorcinol, isoaminile citrate, isosorbide dinitrate, ibuprofen, iodine, iodoform, isoaminile, lidocaine, lopirine, levamisole, methadone, methyprylon, methylphenidate, mephenesin, methylephedrine, meclastine, methopromazine, mesuximide, menthol, methylpentynol, metixene, mesoprostol, nikethamide, norpseudoephedrine, nonylic vanillylamide, oxytetracaine, oxyprenolol, oxyphenbutazone, oxyquinoline, pinene, prolintane, procyclidine, piperazine, pivazide, phensuximide, procaine, phenindamine, promethazine, pentetrazole, profenamine, perazine, phenol, pethidine, pilocarpine, prenylamine, phenoxybenzamine, resochine, scopolamine, salicylic acid, sparteine, timolol, trifluperazine, tetracaine, trimipramine, tranylcypromine, trimethadione, tybamate, thymol, thioridazine, valproic acid and verapamil, and also other active substances familiar to the skilled worker that can be absorbed through the skin, including the mucous membranes. This list is of course not exhaustive.

Particularly important active substances will now be listed and classified in more detail—here again without claiming completeness within the context of the present invention:

| Indication: | Active substance |
|---|---|
| Antimycotics | Naftifine<br>((E)-N-Cinnamyl-N-methyl-1-naphthalenemethanamine) |
| | Amorolfine<br>((±)-cis-2,6-Dimethyl-4-[2-methyl-3-(4-tert-pentylphenyl)propyl]morpholine) |
| | Tolnaftate<br>(O-(2-Naphthyl)-N-methyl-N-m-tolyl-thiocarbamate) |

| Indication: | Active substance |
|---|---|
| | Clotrimazole<br>(1-[(2-Chlorophenyl)diphenylmethyl]-1H-imidazole) |
| Antiseptics | Triclosan |
| | Ethacridine |
| | Chlorhexidine |
| | Hexetidine |
| | Dodicin |
| | Iodine |
| Non-steroidal anti-inflammatory drugs | Methyl salicylate |
| | Etofenamate |
| | Indomethacin<br>([1-(4-Chlorobenzoyl)-5-methoxy-2-methyl-1H-indol-3-yl]acetic acid |
| Antipruritics | Crotamiton |
| Local anesthetics | Benzocaine |
| Antipsoriatics | |
| Keratolytics | Urea |

Further active substances which promote wound healing, such as silver sulfadiazene, can likewise be employed.

With particular advantage and in the context of the invention it is also possible to mention hyperemic active substances such as natural active substances from cayenne pepper or synthetic active substances such as nonivamide, nicotinic acid derivatives, preferably benzyl nicotinate or propyl nicotinate, and antiinflammatories and/or analgesics.

By way of example mention may be made of capsaicin

[8-Methyl-trans-6-nonenoic acid (4-hydroxy-3methoxybenzlamide)]

Nonivamide

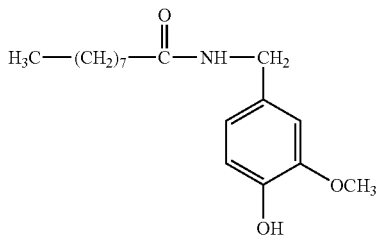

Nicotinic acid benzyl ester

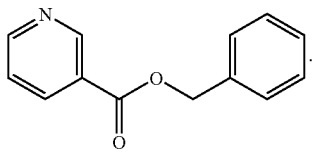

Benzyl nicotinate

Among the active substances, the disinfectants and antiseptics should be emphasized as being particularly important, and so their use is to be emphasized again.

Substances designated disinfectants are those suitable for disinfection, i.e., for controlling pathogenic microorganisms (for example, bacteria, viruses, spores, microfungi and molds), in particular generally by use on the surface of skin, clothing, equipment, rooms, but also drinking water, foodstuffs, seed (dressing) and as soil disinfectants.

Disinfectants particularly for local use, for disinfecting wounds for example, are also referred to as antiseptics.

As an antiseptic use may be made in particular of the lactic acid derivatives, such as esters and also oligolactic and polylactic acid.

Known lactic esters include the esters, frequently named as lactates of the respective alcohol component, of the general formula

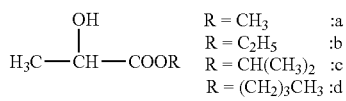

$R = CH_3$ :a
$R = C_2H_5$ :b
$R = CH(CH_3)_2$ :c
$R = (CH_2)_3CH_3$ :d the majority of which are products which have low melting points or are liquid at 20° C. and which, with the exception of the lower alkyl esters, are sparingly soluble in water but readily soluble in alcohol and ether.

The following lactic esters are differentiated:
(a) lactic acid methyl ester (methyl lactate), $C_4H_8O_3$, $M_r$ 104.10, boiling point 145° C.
(b) lactic acid ethyl ester (ethyl lactate), $C_5H_{10}O_3$, $M_r$ 118.13, D. 1.03, boiling point 154° C.
(c) lactic acid isopropyl ester (isopropyl lactate), $C_6H_{12}O_3$, $M_r$ 132.15, D. 0.9980, boiling point 167° C.
(d) lactic acid butyl ester (butyl lactate), $C_7H_{14}O_3$, $M_r$ 146.18, D. 0.9803, boiling point 187° C.

Polylactic acid (polylactide) is a polyester based on lactic acid, from whose lactide it can be prepared by means of ring-opening polymerization.

The active substance fraction in the self-adhesive composition is preferably between 0.001% by weight and 0.7% by weight, more preferably between 0.01% by weight and 0.67% by weight, with particular preference between 0.03% by weight and 0.63% by weight.

Depending on the intended use, suitable web-form backing materials for the self-adhesive compositions processed and produced in accordance with the invention are all known backings, with or without appropriate chemical or physical surface pretreatment of the coating side, and also anti-adhesive physical treatment or coating of the reverse side. Mention may be made, for example, of creped and noncreped papers, polyethylene, polypropylene and mono- or biaxially oriented polypropylene films, polyester, PVC and other films, foam materials in web form, made from polyethylene and polyurethane, for example.

Another suitable example is a metallocene polyethylene nonwoven.

The metallocene polyethylene nonwoven preferably has the following properties:
a basis weight of from 40 to 200 g/m$^2$, in particular from 60 to 120 g/m$^2$, and/or
a thickness of from 0.1 to 0.6 mm, in particular from 0.2 to 0.5, and/or
a lengthwise ultimate tensile stress elongation of from 400 to 700%, and/or
a transverse ultimate tensile stress elongation of from 250 to 550%.

As carrier material it is also possible to use all known textile carriers such as wovens, knits or nonwoven webs; the term "web" embraces at least textile sheetlike structures in accordance with EN 29092 (1988) and also stitchbonded nonwovens and similar systems.

It is likewise possible to use spacer fabrics, including spacer knits, with lamination. Spacer fabrics of this kind are disclosed in EP 0 071 212 B1. Spacer fabrics are matlike layer structures comprising a cover layer of a fiber or filament web, an underlayer and individual retaining fibers or bundles of such fibers between these layers, said fibers being distributed over the area of the layer structure, being needled through the particle layer, and joining the cover layer and the underlayer to one another. As an additional, though not mandatory, feature, the retaining fibers in accordance with EP 0 071 212 B1 comprise inert mineral particles, such as sand, gravel or the like, for example.

The holding fibers needled through the particle layer hold the cover layer and the underlayer at a distance from one another and are joined to the cover layer and the underlayer.

Spacer wovens or spacer knits are described, inter alia, in two articles, namely
an article from the journal "kettenwirk-praxis 3/93", 1993, pages 59 to 63, "Raschelgewirkte Abstandsgewirke" [Raschel-knitted spacer knits]
and
an article from the journal "kettenwirk-praxis 1/94", 1994, pages 73 to 76, "Raschelgewirkte Abstandsgewirke", the content of said articles being included here by reference and being part of this disclosure and invention.

Suitable nonwovens include, in particular, consolidated staple fiber webs, but also filament webs, meltblown webs, and spunbonded webs, which generally require additional consolidation. Possible consolidation methods for webs are mechanical, thermal, and chemical consolidation. Whereas with mechanical consolidations the fibers are held together purely mechanically, usually by entanglement of the individual fibers, by the interlooping of fiber bundles or by the stitching-in of additional threads, it is possible by thermal and by chemical techniques to obtain adhesive (with binder) or cohesive (binderless) fiber-fiber bonds. Given appropriate formulation and an appropriate process regime, these bonds may be restricted exclusively, or at least predominantly, to fiber nodal points, so that a stable, three-dimensional network is formed while retaining the loose, open structure in the web.

Webs which have proven particularly advantageous are those consolidated in particular by overstitching with separate threads or by interlooping.

Consolidated webs of this kind are produced, for example, on stitchbonding machines of the "Malifleece" type from the company Karl Meyer, formerly Malimo, and can be obtained, inter alia, from the companies Naue Fasertechnik and Techtex GmbH. A Malifleece is characterized in that a cross-laid web is consolidated by the formation of loops from fibers of the web.

The carrier used may also be a web of the Kunit or Multiknit type. A Kunit web is characterized in that it originates from the processing of a longitudinally oriented fiber web to form a sheetlike structure which has the heads and legs of loops on one side and, on the other, loop feet or pile fiber folds, but possesses neither threads nor prefabricated sheetlike structures. A web of this kind has been produced, inter alia, for many years, for example on stitchbonding machines of the "Kunitvlies" type from the company Karl Mayer. A further characterizing feature of this web is that, as a longitudinal-fiber web, it is able to absorb high tensile forces in the longitudinal direction. The characteristic feature of a Multiknit web relative to the Kunit is that the web is consolidated on both the top and bottom sides by virtue of double-sided needle punching.

Finally, stitchbonded webs are also suitable as an intermediate for forming an adhesive tape of the invention. A stitchbonded web is formed from a nonwoven material having a large number of stitches extending parallel to one another. These stitches are brought about by the incorporation, by stitching or knitting, of continuous textile threads. For this type of web, stitchbonding machines of the "Maliwatt" type from the company Karl Mayer, formerly Malimo, are known.

Also particularly advantageous is a staple fiber web which is mechanically preconsolidated in the first step or is a wet-laid web laid hydrodynamically, in which between 2% and 50% of the web fibers are fusible fibers, in particular between 5% and 40% of the fibers of the web.

A web of this kind is characterized in that the fibers are laid wet or, for example, a staple fiber web is preconsolidated by the formation of loops from fibers of the web or by needling, stitching or air-jet and/or water-jet treatment.

In a second step, thermofixing takes place, with the strength of the web being increased again by the (partial) melting of the fusible fibers.

The web carrier may also be consolidated without binders, by means for example of hot embossing with structured rollers, with properties such as strength, thickness, density, flexibility, and the like being controllable via pressure, temperature, residence time, and embossing geometry.

For the inventive use of nonwovens, the adhesive consolidation of mechanically preconsolidated or wet-laid webs is of particular interest, it being possible for said consolidation to take place by way of the addition of binder in solid, liquid, foamed or pastelike form. A great diversity of theoretical embodiments is possible: for example, solid binders as powders for trickling in, as a sheet or as a mesh, or in the form of binding fibers. Liquid binders may be applied as solutions in water or organic solvent or as a dispersion. For adhesive consolidation, binder dispersions are predominantly chosen: thermosets in the form of phenolic or melamine resin dispersions, elastomers as dispersions of natural or synthetic rubbers, or, usually, dispersions of thermoplastics such as acrylates, vinyl acetates, polyurethanes, styrene-butadiene systems, PVC, and the like, and also copolymers thereof. Normally, the dispersions are anionically or nonionically stabilized, although in certain cases cationic dispersions may also be of advantage.

The binder may be applied in a manner which is in accordance with the prior art and for which it is possible to consult, for example, standard works of coating or of nonwoven technology such as "Vliesstoffe" (Georg Thieme Verlag, Stuttgart, 1982) or "Textiltechnik-Vliesstofferzeugung" (Arbeitgeberkreis Gesamttextil, Eschborn, 1996).

For mechanically preconsolidated webs which already possess sufficient composite strength, the single-sided spray application of a binder is appropriate for effecting specific changes in the surface properties.

Such a procedure is not only sparing in its use of binder but also greatly reduces the energy requirement for drying. Since no squeeze rolls are required and the dispersion remains predominantly in the upper region of the web material, unwanted hardening and stiffening of the web can largely be avoided.

For sufficient adhesive consolidation of the web carrier, the addition of binder in the order of magnitude of from 1% to 50%, in particular from 3% to 20%, based on the weight of the fiber web, is generally required.

The binder may be added as early as during the manufacture of the web, in the course of mechanical preconsolidation, or else in a separate process step, which may be carried out in line or off line. Following the addition of a binder it is necessary temporarily to generate a state in which the binder becomes adhesive and adhesively connects the fibers—this may be achieved during the drying, for example, of dispersions, or else by heating, with further possibilities for variation existing by way of area or partial application of pressure. The binder may be activated in known drying tunnels, or else, given an appropriate selection of binder, by means of infrared radiation, UV radiation, ultrasound, high-frequency radiation or the like. For the subsequent end use it is sensible, although not absolutely necessary, for the binder to have lost its tack following the end of the web production process.

A further, special form of adhesive consolidation consists in activating the binder by incipient dissolution or swelling. In this case it is also possible in principle for the fibers themselves, or admixed special fibers, to take over the function of the binder. Since, however, such solvents are objectionable on environmental grounds, and/or are problematic in their handling, for the majority of polymeric fibers, this process is not often employed.

Starting materials envisaged for the textile carrier include, in particular, polyester, polypropylene, viscose or cotton fibers. The present invention is, however, not restricted to said materials; rather it is possible to use a large number of other fibers to produce the web, as is evident to the skilled worker without any need for inventive activity.

Moreover, knitted fabrics are also outstandingly suitable. Knitted fabrics are produced from one or more threads or thread systems by intermeshing (interlooping), in contrast to woven fabrics, which are produced by intersecting two thread systems (warp and weft threads), and nonwovens (bonded fiber fabrics), where a loose fiber web is consolidated by heat, needling or stitching or by means of water jets.

Knitted fabrics can be divided into weft knits, in which the threads run in transverse direction through the textile, and warp knits, where the threads run lengthwise through the textile. As a result of their mesh structure, knitted fabrics are fundamentally pliant, conforming textiles, since the meshes are able to stretch lengthways and widthways, and have a tendency to return to their original position. In high-grade material, they are very robust.

Finally, the web-form material may be a material with an antiadhesive coating on both sides, such as a release paper or a release film. If desired, the coated backing material is lined with a further release film or a further release paper.

The thickness of the self-adhesive composition on the web-form material may be between 10 µm and 2,000 µm, preferably between 20 µm and 500 µm, with particular preference between 50 and 400 µm.

DETAILED DESCRIPTION OF THE INVENTION

Example 1

Figure 1:
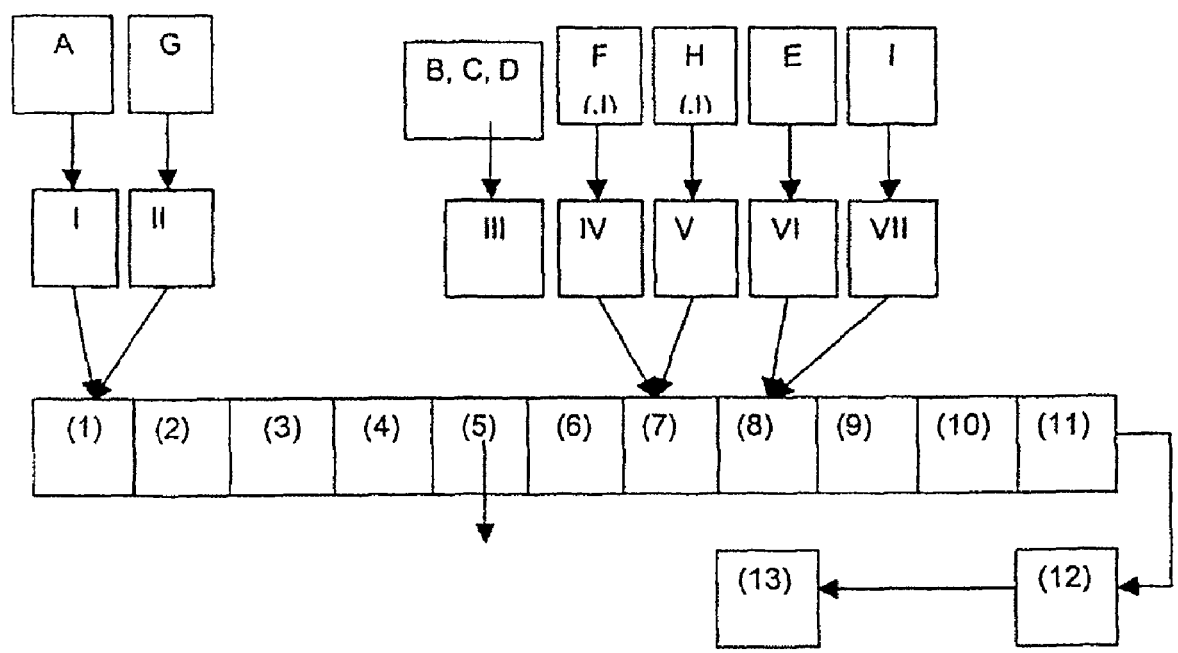
FIG. 1 shows a diagrammatic overview of an apparatus for carrying out the process of the present invention.

A prototype of a self-adhesive composition doped with active substance was prepared solventlessly and continuously using a twin screw extruder, employing the following exemplary formulation (all amounts in parts per hundred (phr) based on the sum of the block copolymer fraction):

A) 100.0 phr A-B/A-B-A block copolymer, consisting of hard and soft segments, with a ratio of A-B-A to A-B of 41:9 and a styrene content of 15% by mass (Vector 4113, Dexco)
B) 21.5 phr hydrocarbon resin (Wingtack 95, Goodyear)
C) 23.9 phr polyterpene resin (Sylvares TR 7115, Arizona Chemical)
D) 17.9 phr rosin ester resin (Staybelite Ester 10, Eastman)
E) 29.9 phr filler (rice flour/iris powder)
F) 9.6 phr paraffinic mineral oil (Ondina 917, Shell Chemicals)
G) 4.8 phr aging inhibitor (Vulkanox BKF, Bayer)
H) 17.9 phr lanolin DAB [German Pharmacopoeia]
I) 13.6 phr capsicum extract as active hyperemic substance, corresponding to 0.3 phr capsaicinoids (calculated as capsaicin)

Example 2

A doped self-adhesive composition was prepared as in example 1 in accordance with the following exemplary formulation (all amounts in parts per hundred (phr) based on the sum of the block copolymer fraction):

A) 100.0 phr A-B/A-B-A block copolymer, consisting of hard and soft segments, with a ratio of A-B-A to A-B of 14:11 and a styrene content of 16% by mass (Kraton D-1113, Kraton)
B) 59.9 phr hydrocarbon resin (Escorez 2203, ExxonMobil)
D) 46.1 phr hydrocarbon resin (Arkon P90, Arakawa)
F) 7.8 phr mineral oil (Whitemor WOM 14, Castrol Ltd.)
G) 3.4 phr aging inhibitor (Irganox 1010, Ciba Specialty Chemicals)
H) 12.2 phr plasticizer (Cetiol V. Henkel KGaA)
J) 0.16 phr nonyl vanillylamide as active substance

Example 3

Another prototype of a self-adhesive composition doped with active substance was prepared solventlessly and continuously by the same procedure as in example 1. In this case the following exemplary formulation was employed (all amounts in parts per hundred (phr) based on the sum of the block copolymer fraction):

A) 100.0 phr A-B/A-B-A block copolymer, consisting of hard and soft segments, with a ratio of A-B-A to A-B of 29:21 and a styrene content of 15% by mass (Vector 4114, Dexco)
C) 22.7 phr hydrogenated hydrocarbon resin (Escorez 5380, ExxonMobil)
D) 55.9 phr hydrogenated rosin (Foral AX-E, Eastman)
F) 7.3 phr mineral oil (Pionier 2071, Hansen&Rosenthal)
G) 2.6 phr aging inhibitor (Lowinox 22M46, Great Lakes Chemical Corp.)
H) 8.9 phr plasticizer (Cetiol V, Henkel KGaA)
I) 18.6 phr capsicum extract as active hyperemic substance, corresponding to 0.4 phr of capsaicinoids (calculated as capsaicin)

Procedure

The prototypes were produced with the aid of a twin screw extruder from Leistritz, having a screw diameter of 50 mm. The backing material was coated using a slot die. FIG. 1 shows a diagrammatic overview of the unit used to carry out the method.

Raw materials A and G were each supplied via a gravimetric metering system (I) and (II) to the filling section of a twin screw extruder.

The material was supplied via a first conveying process zone (1) to further zones (2)-(4), which mixed the material.

In the conveying process zone (5)—depending on formulation—components B/C/D were metered in gravimetrically (III). This was followed by mixing and conveying (6).

Thereafter came zone (7), which conveyed the material and to which components F and—depending on formulation—H, or a homogeneous mixture or solution of H and J, were metered by way of volumetrically operating gear pumps (IV) and (V). Thereafter the material was mixed again.

This was followed by zone (8), which conveyed the material and to which—depending on formulation—component E was metered by way of a gravimetric metering system (VI) and component I by way of a volumetrically operating gear pump (VII).

In zones (9)-(11) the material was mixed and conveyed.

Subsequently the self-adhesive composition was shaped by way of a 350 mm slot die (12) and extruded. Calendering took place in a calender unit (13), along with lamination to two PET films.

The rotary speed of the extruder was between 100 and 150 rpm. At the exit from the extruder the composition had a temperature of between 90° C. and 100° C.

Analysis

From the laboratory specimens, 5 samples in each case with a diameter of 2.2 cm were punched out and investigated for their release behavior on pig's skin.

For this purpose a sample was applied to a section of pig's skin which had been placed on a Franz release vessel. The release vessel was filled with a receptor phase which was temperature-controlled at a constant 35.5° C. and was stirred continuously. After 24 h the level of capsaicinoids in the skin and in the receptor phase was determined quantitatively.

The patch produced from the composition described in example 1 showed effective release of the active substance. Under the conditions specified above, 14 parts per thousand of the active substance were absorbed dermally. The standardized, relative fraction of the dermally absorbed amount is subdivided as follows:

1.6% in the horny layer
44.2% in the epidermis
52.2% in the dermis
2.0% in the receptor phase.

What is claimed is:

1. A process for a solvent-free and mastication-free production of a self-adhesive SBC-based composition which comprises at least one pharmaceutically active substance, in a continuously operating apparatus which comprises a feeding section and a compounding section, said process comprising
   (a) feeding an initial batch which comprises SBC, at least a part of the at least one pharmaceutically active substance and, optionally, at least a part of any further components of the composition into the feeding section of the apparatus;
   (b) transferring the initial batch from the feeding section to the compounding section of the apparatus;
   (c) optionally, adding any remaining part of the at least one pharmaceutically active substance and any remaining part of the further components of the composition which have not been added to the feeding section, to the compounding section;
   (d) treating the composition in the compounding section to prepare a homogeneous self-adhesive composition; and
   (e) discharging the homogeneous self-adhesive composition from the apparatus; a temperature inside the apparatus being not higher than 110° C.

2. The process of claim 1, wherein the further components of the composition are selected from one or more of low molecular weight SBCs, fillers, plasiticizers, tackifiers, resins, release aids and additives.

3. The process of claim 1, wherein the apparatus comprises a twin-screw extruder.

4. The process of claim 3, wherein the twin-screw extruder comprises at least one metering port and at least one degassing port.

5. The process of claim 4, wherein the twin-screw extruder comprises from two to seven metering ports.

6. The process of claim 1, wherein the temperature inside the apparatus is at least 85° C.

7. The process of claim 1, wherein the temperature is not higher than 100° C.

8. The process of claim 1, wherein the at least one pharmaceutically active substance is used in a concentration of from 0.001% to 0.70% by weight, based on the weight of the composition.

9. The process of claim 8, wherein the at least one pharmaceutically active substance is used in a concentration of from 0.01% to 0.67% by weight.

10. The process of claim 9, wherein the at least one pharmaceutically active substance is used in a concentration of from 0.03% to 0.63% by weight.

11. The process of claim 1, wherein the SBC is used in a concentration of from 5% to 90% by weight.

12. The process of claim 10, wherein the SBC is used in a concentration of from 10% to 85% by weight.

13. A process for a solvent-free and mastication-free production of a self-adhesive SBC-based composition which comprises at least one pharmaceutically active substance, in a continuously operating apparatus which comprises a feeding section and a compounding section, said process comprising
   (a) feeding an initial batch which comprises SBC and, optionally, at least a part of any further components of the composition with the exception of the at least one pharmaceutically active substance into the feeding section of the apparatus;
   (b) transferring the initial batch from the feeding section to the compounding section of the apparatus;
   (c) adding the at least one pharmaceutically active substance and, optionally, any remaining part of the further components of the composition which has not been added to the feeding section to the compounding section;
   (d) treating the composition in the compounding section to prepare a homogeneous self-adhesive composition; and
   (e) discharging the homogeneous self-adhesive composition from the apparatus; a temperature inside the apparatus being not higher than 110° C.

14. The process of claim 13, wherein the further components of the composition are selected from one or more of low molecular weight SBCs, fillers, plasiticizers, tackifiers, resins, release aids and additives.

15. The process of claim 13, wherein the apparatus comprises a twin-screw extruder.

16. The process of claim 15, wherein the twin-screw extruder comprises at least one metering port and at least one degassing port.

17. The process of claim 16, wherein the twin-screw extruder comprises from two to seven metering ports.

18. The process of claim 13, wherein the temperature inside the apparatus is at least 85° C.

19. The process of claim 13, wherein the temperature is not higher than 100° C.

20. The process of claim 13, wherein the at least one pharmaceutically active substance is used in a concentration of from 0.001% to 0.70% by weight, based on the weight of the composition.

21. The process of claim 20, wherein the at least one pharmaceutically active substance is used in a concentration of from 0.01% to 0.67% by weight.

22. The process of claim 21, wherein the at least one pharmaceutically active substance is used in a concentration of from 0.03% to 0.63% by weight.

23. The process of claim 13, wherein the SBC is used in a concentration of from 5% to 90% by weight.

24. The process of claim 22, wherein the SBC is used in a concentration of from 10% to 85% by weight.

25. A process for producing a self-adhesive composition on a carrier material, which process comprises carrying out the process of claim 1, transferring the self-adhesive composition to a coating device and thereafter, coating the carrier material with the self-adhesive coating composition.

26. The process of claim 25, wherein the transfer of the coating composition to the coating device involves at least one of a melt pump and an extruder.

27. The process of claim 25, wherein the carrier material comprises a web material.

28. The process of claim 25, wherein the carrier material comprises at least one of a release film and a release paper.

29. The process of claim 28, wherein the process further comprises covering the coated composition with a release film or release paper.

30. The process of claim 25, wherein the coating device comprises an extrusion die.

31. The process of claim 25, wherein the coating device comprises at least one of a roll unit and a calendar unit.

32. The process of claim 31, wherein a coating thickness of the composition is adjusted by allowing it to pass through one or more roll nips of the at least one of a roll unit and a calendar unit.

33. The process of claim 31, wherein the coating device further comprises an extrusion die.

34. The process of claim 25, wherein a thickness of the self-adhesive composition on the carrier material is adjusted to from 10 µm to 2,000 µm.

35. The process of claim 34, wherein the thickness is from 20 µm to 500 µm.

36. The process of claim 35, wherein the thickness is from 50 µm to 400 µm.

37. A process for producing a self-adhesive composition on a carrier material, which process comprises carrying out the process of claim 13, transferring the self-adhesive composition to a coating device and thereafter, coating the carrier material with the self-adhesive coating composition.

38. The process of claim 37, wherein the transfer of the coating composition to the coating device involves at least one of a melt pump and an extruder.

39. The process of claim 37, wherein the carrier material comprises a web material.

40. The process of claim 37, wherein the carrier material comprises at least one of a release film and a release paper.

41. The process of claim 30, wherein the process further comprises covering the coated composition with one of a release film and a release paper.

42. The process of claim 37, wherein the coating device comprises an extrusion die.

43. The process of claim 37, wherein the coating device comprises at least one of a roll unit and a calendar unit.

44. The process of claim 43, wherein a coating thickness of the composition is adjusted by allowing it to pass through one or more roll nips of the at least one of a roll unit and a calendar unit.

45. The process of claim 33, wherein the coating device further comprises an extrusion die.

46. The process of claim 37, wherein a thickness of the self-adhesive composition on the carrier material is adjusted to from 10 µm to 2,000 µm.

47. The process of claim 46, wherein the thickness is from 20 µm to 500 µm.

48. The process of claim 47, wherein the thickness is from 50 µm to 400 µm.

49. The process of claim 1, wherein the at least one pharmaceutically active substance comprises one or more of an antimycotic, an antiseptic, a disinfectant, an antipruritic, a local anaesthetic, a keratolytic, a hyperemic active substance and silver sufadiazene.

50. The process of claim 13, wherein the at least one pharmaceutically active substance comprises one or more of an antimycotic, an antiseptic, a disinfectant, an antipruritic, a local anaesthetic, a keratolytic, a hyperemic active substance and silver sufadiazene.

* * * * *